US00PP37838P2

(12) United States Plant Patent
Davidson

(10) Patent No.: US PP37,838 P2
(45) Date of Patent: Nov. 3, 2026

(54) ***DASIPHORA* PLANT NAMED 'Bailras'**

(50) Latin Name: *Dasiphora fruiticosa*
Varietal Denomination: Bailras

(71) Applicant: His Majesty the Kind in the right of Canada as represented by the minister of Agriculture and Agrifood, Saint-Hyacinthe (CA)

(72) Inventor: Campbell G. Davidson, West Hawk Lake (CA)

(73) Assignee: HIS MAJESTY THE KING IN THE RIGHT OF CANADA AS REPRESENTED BY THE MINISTER OF AGRICULTURE AND AGRIFOOD, Saint-Hyacinthe (CA)

( * ) Notice: Subject to any disclaimer, the term of this patent is extended or adjusted under 35 U.S.C. 154(b) by 0 days.

(21) Appl. No.: 19/630,048

(22) Filed: Mar. 26, 2026

(51) Int. Cl.
*A01H 5/02* (2018.01)
*A01H 6/74* (2018.01)

(52) U.S. Cl.
USPC ..... Plt./237

(58) Field of Classification Search
USPC ..... Plt./237
See application file for complete search history.

(56) References Cited

U.S. PATENT DOCUMENTS

PP30,710 P3 * 7/2019 Wood ..... Plt./357

* cited by examiner

*Primary Examiner* — Susan Mccormick Ewoldt
*Assistant Examiner* — Zachariah Allan Kay
(74) *Attorney, Agent, or Firm* — Penny J. Aguirre

(57) ABSTRACT

A new cultivar of *Dasiphora* plant named 'Bailras' that is characterized by its compact and upright, rounded plant habit, its large leaves that are dark green in color, and its single flowers that open deep pink in color with the color resistant to fading under high heat before fading in late summer to white flushed with pink.

2 Drawing Sheets

Botanical classification: *Dasiphora fruiticosa.*
Variety denomination: 'Bailras'.

BACKGROUND OF THE INVENTION

The present invention relates to a new and distinct cultivar of *Dasiphora fruiticosa*. The new cultivar will be referred to hereafter by its cultivar name, 'Bailras'. 'Bailras' is a new cultivar of deciduous shrub grown for landscape use.

The new cultivar is the result of a controlled breeding program conducted by the Inventor in Morden, MB, Canada. The intent of the breeding program is to develop a new cultivar of *Dasiphora* with flowers that are deep pink in color. 'Bailras' originated as a seedling that arose from a cross made in 2009 between unnamed and unpatented plants of *Dasiphora fruiticosa* from the breeders' program; the female parent designated as accession No. 04221 and the male parent designated as accession No. 98517. 'Bailras' was selected as a single unique plant in 2010 from the resulting seedlings.

Asexual propagation of the new cultivar was first accomplished by softwood stem cuttings under the direction of the Inventor in Cottage Grove, Minnesota in July of 2010. Asexual propagation by softwood stem cuttings has determined that the characteristics of the new cultivar are stable and reproduced true to type in successive generations.

SUMMARY OF THE INVENTION

The following traits have been repeatedly observed and represent the characteristics of the new shrub rose. These attributes in combination distinguish 'Bailras' as a unique cultivar of *Dasiphora.*

1. 'Bailras' exhibits a compact and upright, rounded plant habit.
2. 'Bailras' exhibits large leaves that are dark green in color.
3. 'Bailras' exhibits single flowers that open deep pink in color with the color resistant to fading under high heat before fading in late summer to white flushed with pink.

The female parent of 'Bailras' differs from 'Bailras' in having a low prostrate-type plant habit, pink flowers with white centers that fade to white in mid-summer, and smaller leaves. The male parent of 'Bailras' differs from 'Bailras' in having white and pink flowers that fade in mid-simmer to white. 'Bailras' can be compared to the *Dasiphora* cultivars 'Pink Beauty' (not patented) and 'SMNPPS' (U.S. Plant Pat. No. 30,710). 'Pink Beauty' is similar to 'Bailras' in having an upright rounded plant habit and large leaves. 'Pink Beauty' differs from 'Bailras' in having flowers that are smaller in size, pink flowers that fade faster to white in mid-summer, and foliage that is lighter green in color. 'SMNPPS' is similar to 'Bailras' in having dark green foliage and pink flowers. 'SMNPPS' differs from 'Bailras' in having a smaller plant size and flowers that are pink in color with white centers and smaller in size.

BRIEF DESCRIPTION OF THE DRAWINGS

The accompanying color photographs illustrate the overall appearance and distinct characteristics of the new *Dasi-*

*phora*. The photographs were taken of a 2-year-old plant of 'Bailras' as grown outdoors in a 2-gallon container in Cottage Grove, Minnesota.

Figure 1:
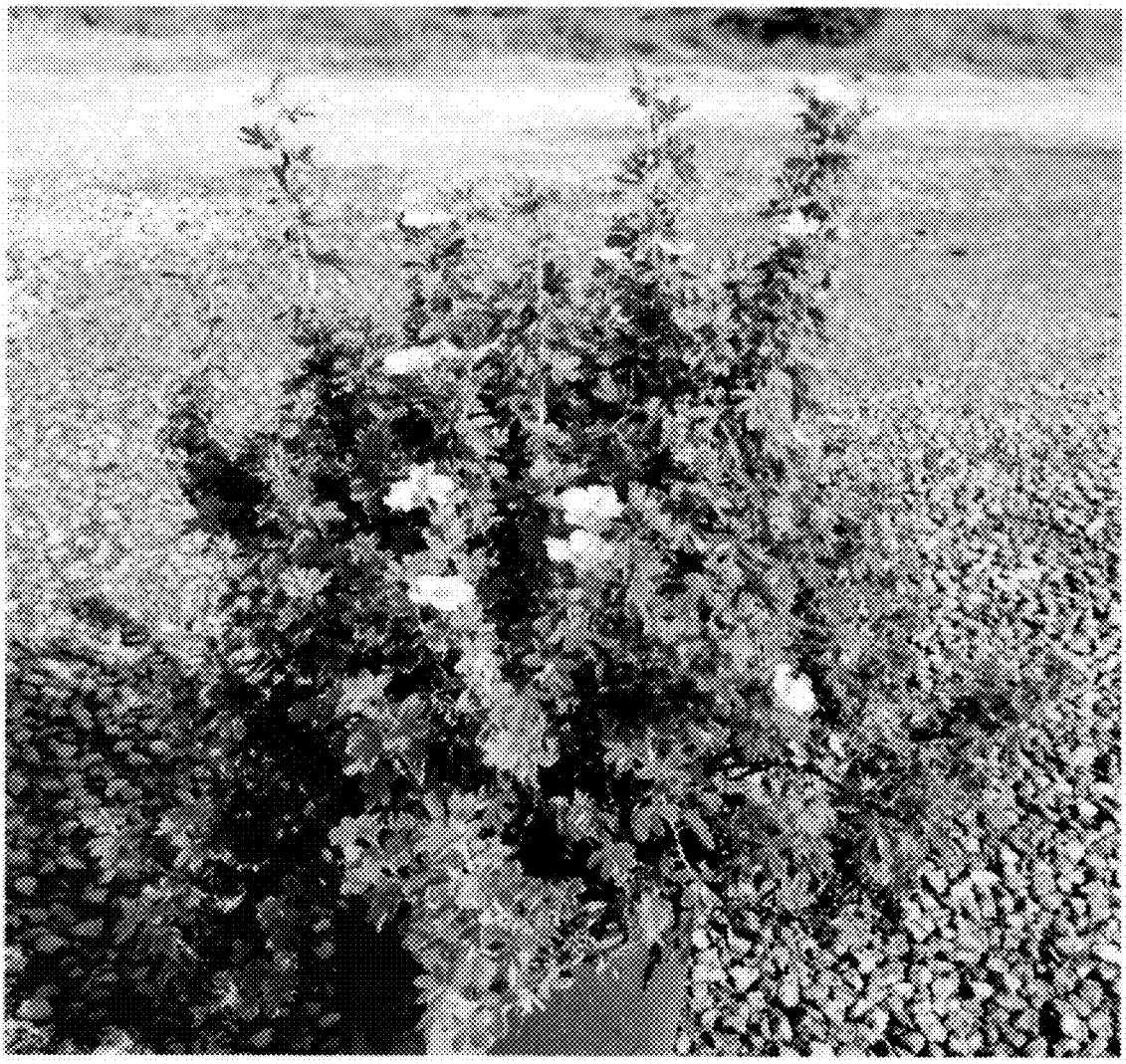

The photograph in FIG. 1 provides a side view of 'Bailras' in bloom.

Figure 2:
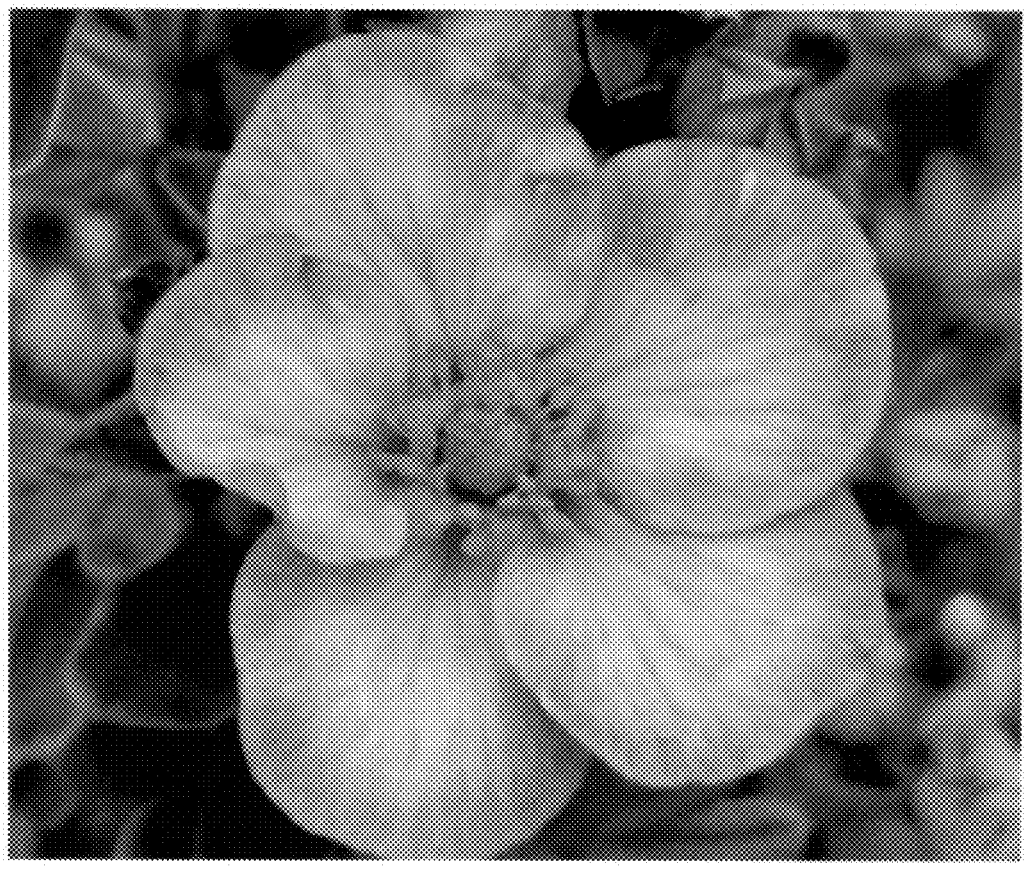

The photograph in FIG. 2 provides a provides a close-up view of a flower of 'Bailras'.

The colors in the photographs are as close as possible with the photographic and printing technology utilized and the color values cited in the detailed botanical description accurately describe the colors of the new *Dasiphora*.

DETAILED BOTANICAL DESCRIPTION

The following is a detailed description of 2-year-old plants of 'Bailras' as grown outdoors in 2-gallon containers in Cottage Grove, Minnesota. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—2 weeks in June and intermittently through September in Minnesota.

*Plant type*.—Deciduous shrub.

*Plant habit*.—Compact, mounded.

*Height and spread*.—An average of 45 cm in height and 50 cm in width as grown in a container, reaches about 91 cm in height and spread as grown in the landscape.

*Hardiness*.—At least in U.S.D.A. Zones 3 to 8.

*Diseases and pests*.—None observed.

*Propagation*.—Softwood stem cuttings.

*Root description*.—Fine, fibrous, 155C and 200B.

*Growth rate*.—Moderate.

*Root development*.—Cuttings initiate roots in 4 weeks and a fully rooted young plant is produced in 60 days.

Branch description:

*Branch shape*.—Rounded.

*Branch color*.—Young and mature; 142C, flushed with 173A, old; 200A and N200B, and 178A.

*Branch surface texture*.—Young and mature; densely covered with long, fine, soft hairs, up to 2 mm in length, ranges between NN155D in color and matching color of branch surface, old; exfoliating, matte.

*Branching*.—Freely branching, outward to upright.

*Branch size*.—An average of 45 cm in length and 3 mm in diameter.

*Branch quantity*.—Average of 40.

*Internode length*.—Average of 2 cm.

Foliage description:

*Leaves*.—Compound, alternate arrangement, reniform in shape, an average of 4 cm in length and 3.5 in width, 60 leaves per branch.

*Leaflets*.—Ranges between 4 and 7, obovate in shape, rounded and apiculate apex, truncate base, entire margins, an average of 2.2 cm in length and 6 mm in width, unlobed, both surfaces matte, slightly rugose, both surfaces densely pubescent with soft tomentose hairs matching leaf surface colors, upper surface color NN137A, lower surface color N148A.

*Stipules*.—Narrow oblong in shape, both sides smooth and glabrous, matte, 7 mm in length, 2 mm in width, top cleft, base narrow cuneate, color both surfaces; 174A.

*Petioles*.—An average of 5 mm in length and 0.8 mm in diameter, medium strength, color; 139D, flushed with 183A, surface is densely covered with long, fine, soft hairs, 1 mm in length, color; NN155D.

Inflorescence description:

*Inflorescence type*.—Solitary, terminal and axillary at upper nodes of stems.

*Flower number*.—An average 1 flower and 5 buds per main stem, 450 flowers and buds per plant.

*Flower fragrance*.—None.

*Flower longevity*.—About 5 days, self-cleaning.

*Flower type*.—Single, rotate.

*Flower aspect*.—Upright to slightly outward.

*Flower size*.—An average of 1.5 cm in diameter and 3 mm in depth.

*Pedicels*.—An average of 1 cm in length, 1 mm in diameter, held vertical, 143D in color, surface is matte, and densely covered with long, fine, soft hairs with a matte appearance, 1.3 mm in length, NN155D in color.

*Flower buds*.—Spherical in shape, flattened, an average of 5 mm in diameter, 3.5 mm in depth, color; 143A, top lightly flushed with 178A, surface is densely covered with long, fine, soft hairs; shiny appearance, 2 mm in length, NN155D in color.

*Sepals*.—5, deltoid in shape, entire margins, 1 cm in length, 4 mm in width, acuminate apex, truncate base, both surfaces matte and densely covered with long, fine, soft hairs; shiny appearance, 1.3 mm in length, NN155D in color, color; both surfaces base 11B, apex 191A, epicalyx; 5-lobed, lanceolate in shape, entire margins, acute apex, an average of 1 cm in length and 4 mm in width, upper and lower surface; 139A in color and very slightly pubescent.

*Petals*.—Average of 5, whorled, orbicular in shape, obtuse apex, cuneate base, margins are entire and slightly undulate, both surfaces are smooth, glabrous, velvety, and matte, color; when opening and fully open upper surface 150D, tips flushed with 63A, when opening and fully open lower surface 150D.

*Receptacle*.—Very densely pubescent, 2 mm in depth, 5 mm in diameter, 144A in color.

Reproductive organs:

*Pistils*.—Average of 50, pilose at base, 4 mm in diameter, stigma; very minute, rounded in shape and less than 0.5 mm in diameter, 23A in color, style; average of 1.4 mm in length, color 23A at the top section and NN155D at the mid-section to base, ovary; superior, 2 mm in diameter and depth, 144A in color.

*Stamens*.—10, filaments; average of 1.8 mm in length, 155A in color, anthers; average of 1 mm in diameter, oblong in shape, 23A in color, pollen; high in quantity, 23A in color.

*Fruit and seed*.—Have not been observed to date.

It is claimed:

1. A new and distinct cultivar of *Dasiphora* plant named 'Bailras' as herein illustrated and described.

* * * * *